United States Patent
Kim et al.

(10) Patent No.: US 12,001,755 B2
(45) Date of Patent: Jun. 4, 2024

(54) APPARATUS AND METHOD FOR CARING EMOTION BASED ON VEHICLE SOUND

(71) Applicants: HYUNDAI MOTOR COMPANY, Seoul (KR); Kia Corporation, Seoul (KR); Seoul National University R&DB Foundation, Seoul (KR)

(72) Inventors: Ki Chang Kim, Suwon-si (KR); Eun Soo Jo, Hwaseong-si (KR); Tae Kun Yun, Anyang-si (KR); Sang Jin Hong, Hwaseong-si (KR); Dong Chul Park, Anyang-si (KR); Kyoung Jin Chang, Suwon-si (KR); Ju In Kim, Yongin-si (KR); Jin Sung Lee, Hwaseong-si (KR); Myung Hwan Yun, Seoul (KR); Sung Ho Kim, Seoul (KR)

(73) Assignees: HYUNDAI MOTOR COMPANY, Seoul (KR); KIA CORPORATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 345 days.

(21) Appl. No.: 17/512,070

(22) Filed: Oct. 27, 2021

(65) Prior Publication Data
US 2022/0357912 A1    Nov. 10, 2022

(30) Foreign Application Priority Data
May 10, 2021    (KR) ................ 10-2021-0060247

(51) Int. Cl.
*G06F 3/16*    (2006.01)
*A61B 5/16*    (2006.01)
(Continued)

(52) U.S. Cl.
CPC .............. *G06F 3/165* (2013.01); *A61B 5/165* (2013.01); *A61B 5/18* (2013.01); *G05B 13/027* (2013.01); *G07C 5/085* (2013.01); *G06V 20/597* (2022.01)

(58) Field of Classification Search
None
See application file for complete search history.

(56) References Cited

U.S. PATENT DOCUMENTS 9,934,667 B1 *    4/2018    Fields ................ G08B 21/02
2017/0315987 A1 *    11/2017    Srinivasan .......... G06F 40/35
(Continued)

FOREIGN PATENT DOCUMENTS

KR    10-1724334 B1    4/2017
KR    10-2060100 B1    12/2019
(Continued)

OTHER PUBLICATIONS

D. Hazarika et al., Conversational Memory Network for Emotion Recognition in Dyadic Dialogue Videos, Proc. of NAACL_HLT 2018, pp. 2122-2132 (New Orleans, LA, Jun. 1-6, 2018) (Year: 2018).*

*Primary Examiner* — Walter F Briney, III
(74) *Attorney, Agent, or Firm* — MORGAN, LEWIS & BOCKIUS LLP

(57) ABSTRACT

An apparatus and a method for caring emotion of a driver based on a vehicle sound, may include a detector configured to detect driving information of the vehicle and body information of a user, a non-transitory storage to store instructions, and a processor to execute the instructions. The processor determines an emotional status of the driver by use of at least one of the driving information or the body information, to generate a healing sound by designing a virtual sound based on the driving information and the (Continued)

emotional status of the driver, and to generate and output the healing sound.

20 Claims, 7 Drawing Sheets

(51) Int. Cl.
*A61B 5/18* (2006.01)
*G05B 13/02* (2006.01)
*G06V 20/59* (2022.01)
*G07C 5/08* (2006.01)

(56) References Cited

U.S. PATENT DOCUMENTS

2021/0007679 A1  1/2021  Kim et al.
2022/0355732 A1  11/2022  Kim et al.

FOREIGN PATENT DOCUMENTS

KR         10-2179661  B1    11/2020
KR    10-2021-0007635  A     1/2021
KR    10-2022-0150692  A    11/2022

\* cited by examiner

| Vehicle | Q1 | Q2 | Q3 | AVG | Rank |
|---|---|---|---|---|---|
| Sound A | 2.45 | 3.91 | 3.55 | 3.30 | 9 |
| Sound B | 3.27 | 4.09 | 3.55 | 3.64 | 7 |
| Sound C | 2.55 | 3.45 | 3.27 | 3.09 | 11 |
| Sound D | 3.64 | 3.91 | 4.27 | 3.94 | 3 |
| Sound E | 3.91 | 3.64 | 3.82 | 3.79 | 5 |
| Sound F | 3.91 | 4.36 | 4.36 | 4.21 | 1 |
| Sound G | 3.18 | 4.18 | 4.09 | 3.82 | 4 |
| Sound F | 3.73 | 2.91 | 3.09 | 3.24 | 10 |
| Sound G | 3.45 | 4.36 | 4.45 | 4.09 | 2 |
| Sound H | 3.64 | 3.73 | 3.82 | 3.73 | 6 |
| Sound I | 3.82 | 3.36 | 3.27 | 3.48 | 8 |
| Sound J | 3.73 | 3.82 | 3.36 | 3.64 | 7 |

Fig.5

APPARATUS AND METHOD FOR CARING EMOTION BASED ON VEHICLE SOUND

CROSS-REFERENCE TO RELATED APPLICATION

The present application claims priority to Korean Patent Application No. 10-2021-0060247, filed on May 10, 2021, the entire contents of which is incorporated herein for all purposes by this reference.

BACKGROUND OF THE INVENTION

Field of the Invention

The present invention relates to an apparatus and a method for caring emotion based on a vehicle sound.

Description of Related Art

A health care system employs a technology of detecting a driver condition to provide a guide and an alert while inducing driving safety in link to a vehicle system. The health care system collects biometric information, for example, an electrocardiogram, a heart rate, and a driver movement using sensors to determine the driver condition. In addition, the health care system recognizes the facial expression of the driver using a camera to determine an emotional status of the driver.

The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing an apparatus and a method for caring emotion of a driver based on a vehicle sound, configured for recognizing an emotional status of a driver based on driving information of the vehicle and body information of a user, and of controlling a sense output based on the recognized emotional status to provide an emotion care solution.

The technical problems to be solved by the present inventive concept are not limited to the aforementioned problems, and any other technical problems not mentioned herein will be clearly understood from the following description by those skilled in the art to which various exemplary embodiments of the present invention pertains.

According to various aspects of the present invention, an apparatus of caring emotion based on a vehicle sound includes a detector configured to detect driving information of the vehicle and body information of a user, a non-transitory storage to store instructions, and a processor to execute the instructions. The processor determines an emotional status of the driver by use of at least one of the driving information or the body information, to generate a healing sound by designing a virtual sound based on the driving information and the emotional status of the driver, and to output the healing sound.

The processor performs emotion modeling for modeling the emotion of the driver by utilizing a deep learning-based emotion analyzing algorithm.

The deep learning-based emotion analyzing algorithm is designed based on a conversational memory network (CMN).

The processor generates three emotion models by applying previously extracted personalized topics and emotions derived by the deep learning-based emotion analyzing algorithm, and derives emotion adjectives based on the generated three emotion models.

The personalized topics are extracted by utilizing a Latent Dirichelt Allocation (LDA) algorithm.

The processor derives the emotion adjectives using a Latent Semantic Analysis (LSA) algorithm and a Girvan-Newman algorithm.

The processor analyzes an emotion index based on the driving information and the emotion adjectives and drives the emotion correlation equation.

The processor analyzes the emotion index using a convolutional neural network (CNN) algorithm.

The processor re-designs the virtual sound by utilizing the emotion correlation equation as feedback information.

The emotion correlation equation is determined through a Multiple Regression Analysis (MRA) algorithm.

The processor performs at least one of vibration output, scent output, or light driving, in link to the healing sound.

According to exemplary embodiments of the present invention, a method for caring emotion based on a vehicle sound includes detecting driving information of the vehicle and body information of a user, determining an emotional status of the driver by use of at least one of the driving information or the body information, generating a healing sound by designing a virtual sound based on the driving information and the emotional status of the driver, and generating the healing sound.

The method for caring the emotion further includes performing emotion modeling for modeling the emotion of the driver by utilizing a deep learning-based emotion analyzing algorithm.

The performing of the emotion modeling includes extracting personalized topics by utilizing a Latent Dirichelt Allocation (LDA) algorithm, deriving emotions by analyzing the emotion by an emotion classifier based on the personalized topics, generating three emotion models by applying the personalized topics and the emotions, and deriving an emotion adjective based on the generated three emotion models.

The deriving of the emotion adjective includes deriving the emotion adjectives using a Latent Semantic Analysis (LSA) algorithm and a Girvan-Newman algorithm.

The method for caring the emotion further includes deriving an emotion correlation equation by analyzing an emotion index based on the driving information and the emotion adjective.

The deriving of the emotion correlation equation includes analyzing the emotion index using a convolutional neural network (CNN) algorithm.

The generating of the healing sound includes designing the virtual sound by utilizing the emotion correlation equation as feedback information.

The designing of the virtual sound includes performing at least one of pitch control, gain control, an APS control, frequency filtering, shepard layer control, or volume control for the virtual sound.

The method for caring the emotion further includes performing at least one of vibration output, scent output, or light driving, in link to the healing sound.

The methods and apparatuses of the present invention have other features and advantages which will be apparent from or are set forth in more detail in the accompanying

BRIEF DESCRIPTION OF THE DRAWINGS

FIG. 5 is a view exemplarily illustrating emotion evaluated, according to various exemplary embodiments of the present invention;

Figure 1:
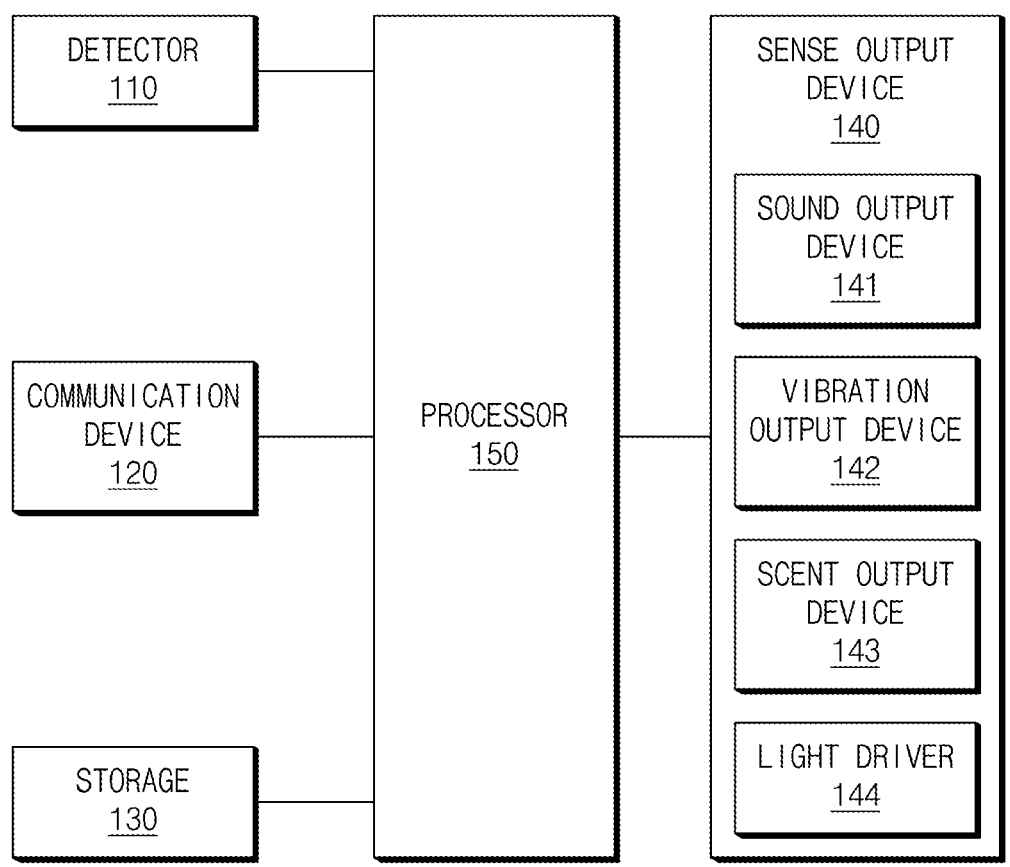
FIG. 1 is a block diagram illustrating an apparatus of caring emotion of a driver based on a vehicle sound, according to various exemplary embodiments of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent portions of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Hereinafter, various exemplary embodiments of the present invention will be described in detail with reference to accompanying drawings. In adding the reference numerals to the components of each drawing, it may be noted that the identical or equivalent component is designated by the identical numeral even when they are displayed on other drawings. Furthermore, in the following description of various exemplary embodiments of the present invention, a detailed description of well-known features or functions will be ruled out in order not to unnecessarily obscure the gist of the present invention.

In describing the components of the exemplary embodiment according to various exemplary embodiments of the present invention, terms such as first, second, "A", "B", "(a)", "(b)", and the like may be used. These terms are merely intended to distinguish one component from another component, and the terms do not limit the nature, sequence or order of the constituent components. Furthermore, unless otherwise defined, all terms used herein, including technical or scientific terms, have the same meanings as those generally understood by those skilled in the art to which various exemplary embodiments of the present invention pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

FIG. 1 is a block diagram illustrating an apparatus of caring emotion of a driver based on a vehicle sound, according to various exemplary embodiments of the present invention.

The apparatus 100 for caring emotion based on the vehicle sound may be mounted in an electrification vehicle such as an electric vehicle (EV), a plug-in hybrid vehicle (PHEV), or a hybrid vehicle (HEV). The electric vehicle may artificially generate a virtual sound (e.g., a virtual engine sound) to prevent a collision with a guardian. The apparatus 100 may implement an emotion care solution by designing the virtual sound (the vehicle sound) based on the emotion of a driver to provide a healing sound customized for the driver. Referring to FIG. 1, the apparatus 100 may include a detector 110, a communication device 120, a storage 130, a sense output device 140, and a processor 150.

The detector 110 may detect driving information of the vehicle and body information of a user of the driver. The detector 110 may detect the driving information, such as a vehicle speed, revolutions per minute (RPM) of a motor, an accelerator pedal opening amount, an accelerator pedal response, lane departure, vehicle collision, and/or inter-vehicle distance, by use of sensors and/or an electric control unit (ECU) mounted in the vehicle. The sensor may include a wheel speed sensor, an Advanced Driver Assistance System (ADAS) sensor, a 3-axis accelerometer, and/or an Inertial Measurement Unit (IMU). The ECU may include a Motor Control Unit (MCU) and/or a Vehicle Control Unit (VCU).

The detector 110 may detect the body information, such as a voice and/or face of the driver by use of a microphone, a camera, and/or a temperature sensor. The detector 110 may detect a voice signal (voice information) uttered by the driver (speaker) through the microphone. The detector 110 may change the voice information into text information through a voice recognition technology. The detector 110 may detect audio information, such as coughing, laughing, crying, and/or shouting, from the voice. The detector 110 may detect the facial expression information by recognizing the face of the driver through the camera. The detector 110 may detect information on body temperature of the driver by use of the temperature sensor.

The communication device 120 may support the apparatus 100 to make communicate with the ECU mounted in the vehicle and/or an external electronic device (e.g., a terminal, or a server). The communication device 120 may include a wireless communication circuit (e.g., a cellular communication circuit, a short-range radio communication circuit, and/or a global navigation satellite system (GNSS) communication circuit), a wired communication circuit (e.g., a local area network (LAN) communication circuit and/or a power line communication circuit), or a vehicle communication circuit (e.g., a controller area network (CAN) communication circuit, a local interconnect network (LIN) communication circuit, and/or an Ethernet communication circuit).

The storage 130 may store an emotion recognizing model, an emotion correlation equation, a sound design algorithm, a virtual sound(s), a healing sound, and/or various setting information. The storage 130 may be a non-transitory storage medium which stores instructions executed by the processor 150. The storage 130 may include at least one of storage media, such as a Random Access Memory (RAM), a Static Random Access Memory (SRAM), a Read Only Memory (ROM), a Programmable Read Only Memory (PROM), an Electrically Erasable and Programmable ROM (EEPROM), an Erasable and Programmable ROM (EPROM), a Hard Disk Drive (HDD), a Solid State Disk (SSD), an embedded multimedia card (eMMC), and/or a universal flash storage (UFS).

The sense output device 140 may output at least one of auditory information (e.g., sound), tactile information (e.g., vibration), olfactory information (e.g., scent), and/or visual information (e.g., light). The sense output device 140 may include a sound output device 141, a vibration output device 142, a scent output device 143, and a light driver 144.

The sound output device 141 may reproduce a virtual sound and/or a healing sound in a response to an instruction of the processor 150 and output the virtual sound and/or the healing sound to the interior and exterior of the vehicle. The sound output device 141 may include a digital signal processor (DSP) and/or microprocessors. The sound output device 141 may output the virtual sound and/or the healing sound to a speaker (e.g., a 3-way speaker and a five-way speaker) mounted inside the vehicle. The sound output device 141 may output the virtual sound and/or the healing sound to speakers (e.g., an external amplifier) outside mounted the vehicle.

The vibration output device 142 may implement tactile information by controlling a vibrator. The vibrator may be mounted on a steering wheel, a cushion of a seat, a backrest, and/or a leg rest, and a plurality of vibrators may be mounted at different positions. The vibration output device 142 may adjust vibration intensity, a vibration direction, a vibration frequency, and/or an amount of vibration under the control of the processor 150.

The scent output device 143 may spray the fragrance under the control of the processor 150. The scent output device 143 may adjust the type of scent and/or a sprayed amount of scent. The scent output device 143 may include a storage container to store scent in a form of liquid or solid.

The light driver 144 may drive lights mounted inside and outside the vehicle. The light driver 144 may adjust the color and/or brightness of the light depending on the instructions of the processor 150.

The processor 150 may control the overall operation of the apparatus 100. The processor 150 may be implemented with at least one of processing units of an Application Specific Integrated Circuit (ASIC), a Digital Signal Processor (DSP), Programmable Logic devices (PLDs), Field Programmable Gate Arrays (FPGAs), a Central Processing unit (CPU), microcontrollers, and/or microprocessors.

The processor 150 may reproduce and output the virtual sound set by a user (e.g., a driver) while driving a vehicle. The virtual sound may include a new sound, a dynamic sound, and/or a futuristic sound. The processor 150 may generate the virtual sound appropriate to a driving situation (driving environment). The processor 150 may adjust and generate the virtual sound based on preset sound design information. The processor 150 may perform pitch control, gain control, an APS control, frequency filtering, shepard layer control, and/or volume (volume) control for the virtual sound. The pitch control is to adjust the pitch of a note, and the gain control is to change the tone and adjust the resistance. The APS control is to adjust the APS resistance, that is, a reaction degree (response) based on the depressing of the accelerator pedal press, and the frequency filtering is to adjust a reproduction frequency band of the sound. The shepard layer control is to generate a second sound source and to adjust the control area of the sound source.

The processor 150 may determine (recognize) the emotional status of the driver by use of at least one of the driving information and the body information detected by the detector 110. The processor 150 may analyze the driving pattern of the driver based on the driving information. The processor 150 may determine the emotional status of the driver, based on the driving pattern and the body information. The processor 150 may determine the emotional status of the driver by use of a deep learning-based emotion recognizing model which is to recognize emotion based on a deep learning algorithm. The emotional status may be classified into positive emotions and negative emotions. The deep learning-based emotion recognizing model may be designed based on a conversational memory network (CNN).

For another example, the processor 150 may recognize a voice uttered by the driver and may extract an emotion word (emotion adjective) related with a virtual sound, from the recognized voice. The processor 150 may determine the emotional status of the driver as being positive emotion or negative emotion, based on the extracted emotion word. For example, the processor 150 may determine the emotion of the driver as being the positive emotion when the extracted emotion word is a positive emotion word, and may determine the emotion of the driver as being the negative emotion, when the extracted emotion word is the negative emotion word.

The processor 150 may generate a healing sound by designing a virtual sound based on the driving information and the emotional status of the driver. The processor 150 may generate the healing sound by adjusting a sound volume, a tone, a reaction degree of an APS, a reproduction frequency band, and/or a sound pitch of the virtual sound.

The processor 150 may output the healing sound to the interior and/or the exterior of the vehicle through the sound output device 141. The sound output device 141 may reproduce the healing sound to output the healing sound to embedded speakers or external speakers. The processor 150 may control vibration, scent, and light in link to the healing sound.

The processor 150 may determine the change in the emotional status of the driver, after outputting the healing sound. The processor 150 may determine the driver as being healed when the emotional status of the driver is changed from the negative emotion to the positive emotion. The processor 150 may analyze an emotion index of the driver for the healing sound and determine an emotion correlation equation, when the emotional status of the driver stays in the negative emotion. The processor 150 may re-design a virtual sound by utilizing the emotion correlation equation as feedback information. Accordingly, the processor 150 may implement an emotion caring service customized for the driver.

Figure 2:
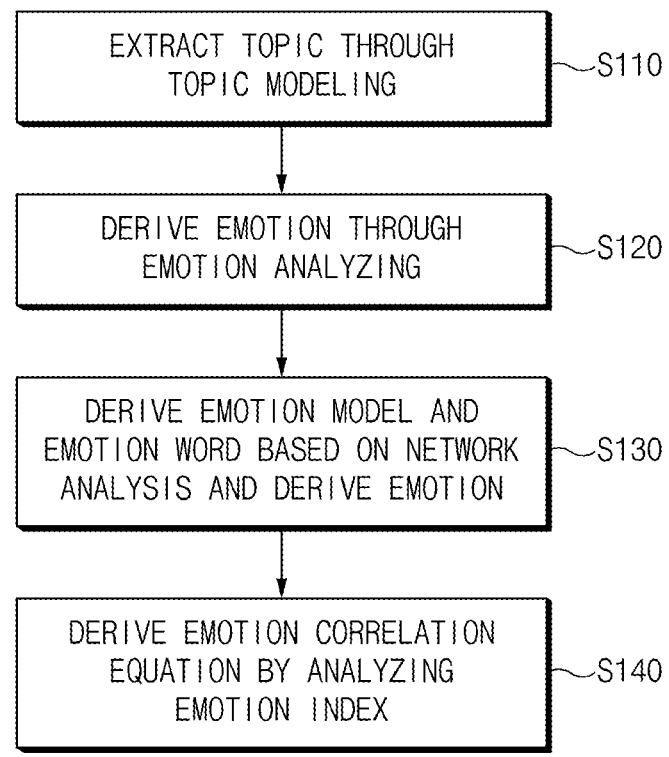
FIG. 2 is a view exemplarily illustrating the procedure of implementing an emotion recognizing model, according to various exemplary embodiments of the present invention.
Figure 3:
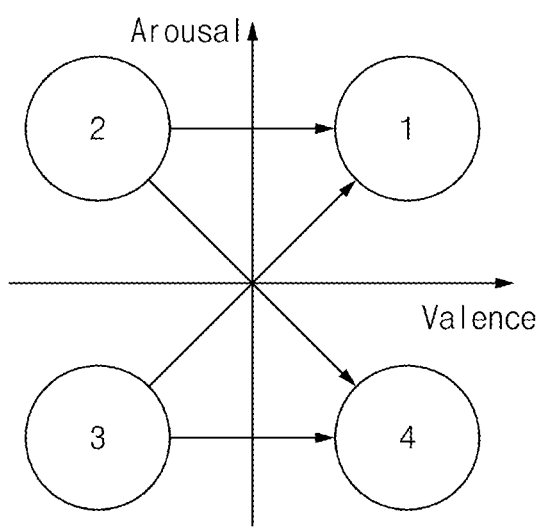
FIG. 3 is a view exemplarily illustrating four patterns of an emotion analyzing model based on a deep learning algorithm, according to various exemplary embodiments of the present invention.
Figure 4:
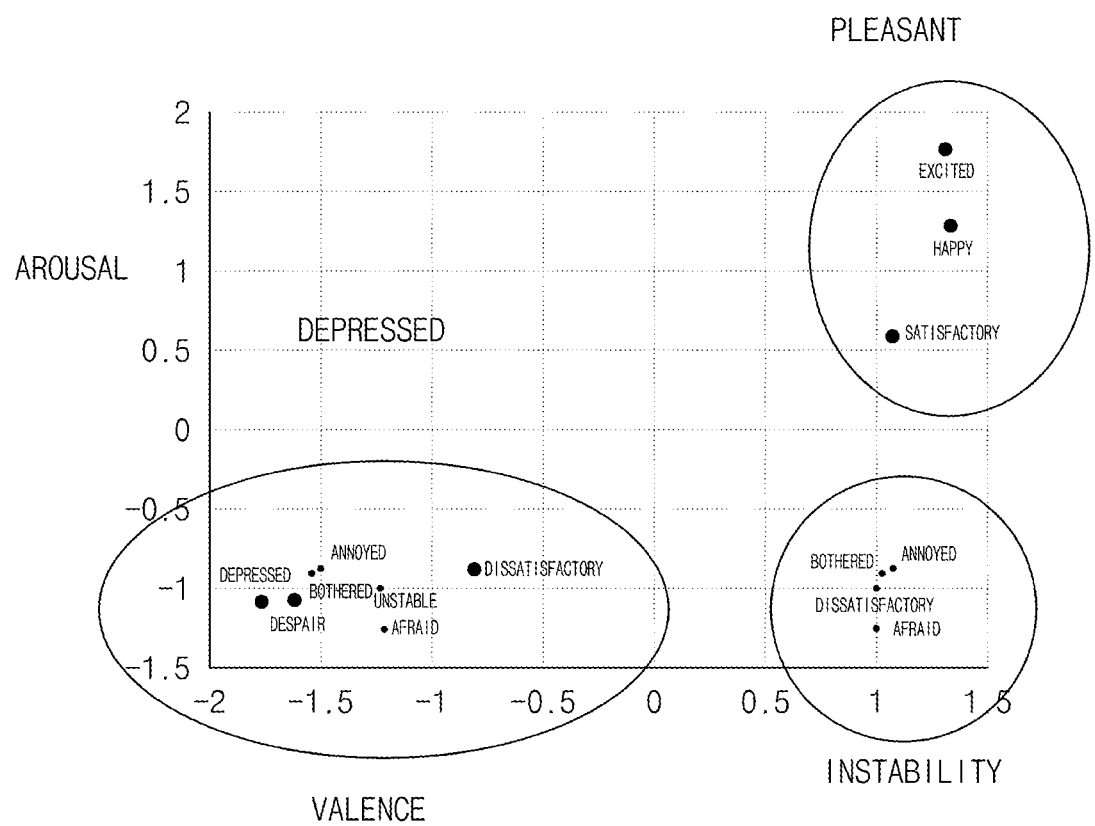
FIG. 4 is a view exemplarily illustrating the correlation between four output values of an emotion analyzing model and emotion determined based on a vehicle environment, according to exemplary embodiments of the present invention.

FIG. 2 is a view exemplarily illustrating the procedure of implementing an emotion recognizing model, according to various exemplary embodiments of the present invention, FIG. 3 is a view exemplarily illustrating four patterns of an emotion analyzing model based on a deep learning algorithm, according to various exemplary embodiments of the present invention, FIG. 4 is a view exemplarily illustrating the correlation between four output values of an emotion analyzing model and emotion determined based on a vehicle environment, according to exemplary embodiments of the present invention, and FIG. 5 is a view exemplarily illustrating emotion evaluated, according to various exemplary embodiments of the present invention.

A computing system (e.g., a server) may implement an emotion recognizing model by performing topic modeling, emotion analyzing, network analyzing, and subject analyzing. The computing system may apply the implemented emotion recognizing model to an actual vehicle.

A processor of the computing system may extract a personalized topic through the topic modeling (S110). The processor may collect online and offline review data related to a vehicle sound, that is, a virtual sound. The processor may extract a virtual sound-related topic from the collected review data through a latent dirichelt allocation (LDA) algorithm. The LDA algorithm is a topic modeling technique that extracts a topic by evaluating the probability that a word is present in a specific topic and the probability that the specific topic is present in data (e.g., review data), as a combined probability. When the topic is extracted, three topics, such as "quietness", "noise", and "sound system" having different characteristics without overlapping between the topics may be extracted. The processor may output keywords grouped into three topics as illustrated in [Table 1] through the topic modeling.

TABLE 1

| Topic | Keyword |
| --- | --- |
| Quietness | Quiet, smooth, comfortable, silent |
| Noise | Noise, road, wind, or tire |
| Sound system | Sound, system, bose, or stereo |

The processor may determine an emotion through the emotion analyzing (S120). The processor may receive, as an input, a keyword grouped with the topic of "sound system" of the extracted personalization topics. Furthermore, the processor may receive voice information related to the topic of "sound system". The processor may analyze emotion by use of an emotion classifier. The processor may determine a total of seven emotions of one positive emotion, one neutral emotion, and five negative emotions through the emotion analyzing. The processor may perform an emotion model and determine an emotion word, through the network analyzing (S130). The processor may determine three emotion models and emotion adjectives by applying three topics extracted from S110 and seven emotions determined from S120. The processor performs the network analyzing based on a deep learning-based emotion analyzing algorithm to generate three emotion models, and may determine emotion adjectives based on the generated three emotion models. The deep learning-based emotion analyzing algorithm is to encode voice information uttered by a speaker by use of a Gated Recurrent Unit (GRU) and to determine emotion through a memory-operation with a target sentence. The deep learning-based emotion analyzing algorithm may be designed based on a conversational memory network (CMN).

The processor may receive, as the body information, audio data, which is for analyzing emotion temporarily uttered, and text data during a conversation for conversation-based emotion classification. The processor may generate a pleasant emotion model (a first emotion model), an unstable emotion model (a second emotion model), and a depressed emotion model (a third emotion model) based on the received body information. To develop an emotion analyzing model, the correlation between personal taste and music preference is first modeled, and the emotion recognizing algorithm may be generated based on the voice of the driver. The emotion analyzing model may be analyzed to four output values (patterns) based on the correlation between the personal taste and the music preference, as illustrated in FIG. 3. When the four output values for a music-based emotion model are applied to an emotion model based on a vehicle environment, the four output values may be re-established to three factors based on "valence" and "arousal". In the instant case, the third factors may include a Comfort Automobilist (first factor), an Adventure Futurist (second factor), and a Technology Enthusiast (third factor). The first factor is the type of a driver who prefers quiet and stable driving, the second factor is the type of a driver who expects a new sound and novel driving experience, and the third factor is the type of a driver who wants to express individuality with a detailed sense.

The three emotion models may be implemented by reflecting "valence" and "arousal", based on the correlation between the four output values of the emotion mode and the emotion determined based on a vehicle environment. Referring to FIG. 4, in the correlation between the four output values for the emotion model and the emotion determination for the vehicle environment, No. 1 corresponds to pleasant emotion, No. 2 and No. 4 correspond to unstable emotion, and No. 3 corresponds to depressed emotion. When the emotion is changed from the negative emotion of No. 2 or No. 3 to the positive emotion of No. 1 or No. 4, respectively, the process may recognize the driver as being healed. In other words, when the emotional status of the driver for the healing sound corresponds to No. 2 or No. 3, the emotional status of the driver is the negative emotion. When the emotional status of the driver for the healing sound is shifted No. 1 or No. 4, the driver is determined as being healed.

The processor may determine emotional adjectives of general emotional vocabulary, comparative emotional vocabulary, and reactive emotional vocabulary, based on the first emotion model, the second emotion model, and the third emotion model. The processor may determine the emotional adjective through a Latent Semantic Analysis (LSA) algorithm and a Girvan-Newman algorithm.

TABLE 2

| Vocabulary | Emotional adjective |
| --- | --- |
| General emotion | loud, rough, sharp, powerful, comfortable, soft, full, light, solid |
| Comparative emotion | modern, stylish, intelligent, alien, futuristic, quiet, smooth, ghostly |
| Reactive emotion | responsive, zippy, agile, fast, instant |

The processor may determine an emotional correlation equation by analyzing an emotion index based on an emotion model and an emotion adjective. The processor may analyze the emotion index, which is based on a sound resulting from positive and negative emotions, based on the emotion model. The processor may receive the driving information and the emotion adjective and may output emotion evaluation scores Q1, Q2, and Q3 by analyzing subjects. The processor may analyze the subject using a CNN algorithm. The processor may determine the emotional correlation equation between the three virtual sounds and the emotion index by analyzing the emotional index. The emotional correlation equation may be utilized as feedback information and used to form a satisfaction index. The processor 150 may perform an emotion evaluation operation for the virtual sound by analyzing the emotion index based on the driving information and the emotional adjectives. The processor 150 may perform the emotion evaluation operation for the following three pragmatic quality items.

[Evaluation Items]

Q1 (Suitable): This is a standard to evaluate the suitability of an electric vehicle sound for a vehicle to determine whether the electric vehicle sound is applicable to the vehicle. This standard is related to the actual applicability for the vehicle.

Q2 (Clear): This is a standard to evaluate whether a clear sound feedback matched with a vehicle deceleration feeling is present, in relation with the travelling performance of the electric vehicle, and is a standard related to a vehicle acceleration feeling.

Q3 (Aware): This is a standard to evaluate whether a sound of an electric vehicle smoothly expresses the travelling status regardless of a surrounding noise, and a standard related to a vehicle status.

As illustrated in FIG. 5, emotion evaluation may be performed with respect to "Suitable" (Q1), "Clear" (Q2), and "Aware" (Q3), and a sound the most excellently representing the satisfactory of the driver may be selected by statistically analyzing the results of the emotion evaluation.

To determine the emotion correlation equation, factor analysis, variance analysis, regression analysis, and statistical analysis process are performed. The factor analysis process is a process of deriving an emotion word, and verifying reliability and suitability. The variance analysis process is a process for user analysis and driver pattern analysis for the emotion word. The regression analysis process is a process to determine an emotion (input value) for a vehicle sound, which affects the satisfaction (output value). The statistical analysis process is a process of deriving a meaningful result by utilizing an emotional index.

The emotion correlation equation may be determined through Multiple regression analysis and may be expressed as in Equation 1.

$$\text{Satisfaction} = 4.202 + 1.109\text{Refined}(\text{Factor 1}) + 0.352\text{Sporty}(\text{Factor 2}) + 0.321\text{Futuristic}(\text{Factor 3}) \quad \text{Equation 1}$$

In the instant case, "Satisfaction" is assumed to be a perfect score of "7", which is adjustable. Factor 1 may be an emotional evaluation score for refined characteristics of vehicle sound, Factor 2 may be an emotional evaluation score for sporty characteristics, and Factor 3 may be an emotional evaluation score for future-oriented characteristics.

The processor 150 may predict satisfaction with the virtual sound by use of the emotional correlation equation. The processor 150 may determine (predict) satisfaction by substituting the input emotional evaluation into the emotion correlation equation when emotional evaluation for refined characteristics, sporty characteristics, and future specific of the virtual sound is input.

Figure 6:
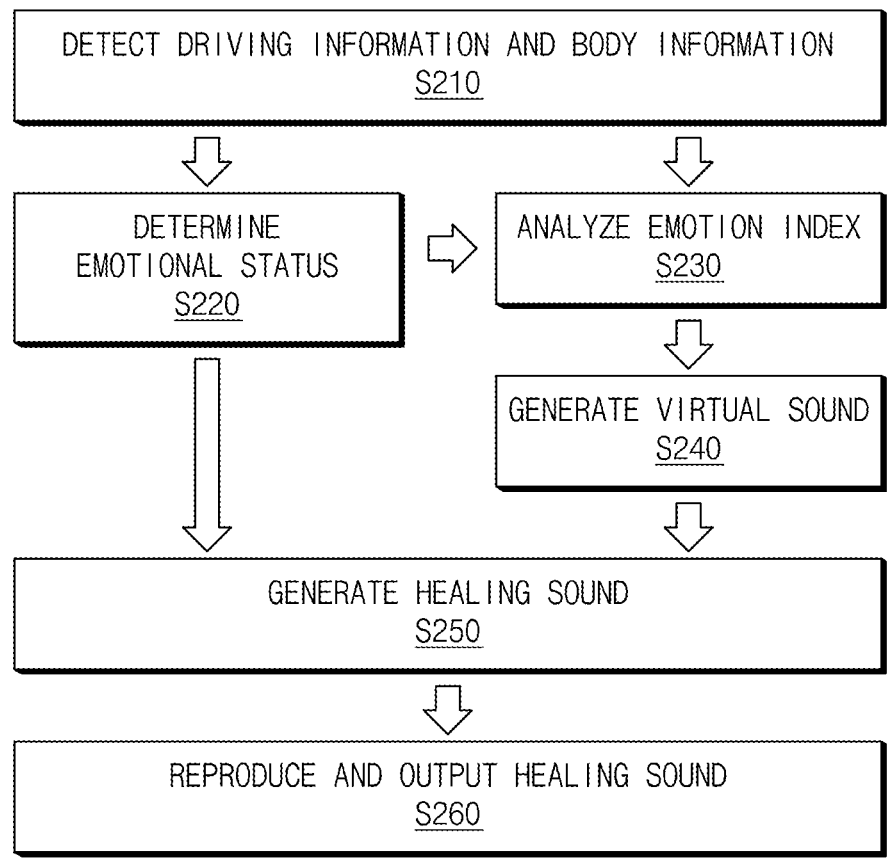
FIG. 6 is a flowchart illustrating an apparatus of caring emotion of a driver based on a vehicle sound, according to various exemplary embodiments of the present invention.

FIG. 6 is a flowchart illustrating an apparatus of caring emotion of a driver based on a vehicle sound, according to various exemplary embodiments of the present invention.

The processor 150 may detect driving information of the vehicle and body information of a user (S210). The processor 150 may detect the driving information, such as, slow acceleration, rapid acceleration, accelerator pedal response, lane departure, front/rear collision, or inter-vehicle distance through the detector 110. The processor 150 may detect the face and the voice of the driver through the camera and/or the microphone.

The processor 150 may determine the emotional status of the driver, based on at least one of the driving pattern or body information (S220). The processor 150 may determine the emotional status of the driver based on the surrounding environment through emotion modeling.

The processor 150 may analyze an emotion index (S230). The processor 150 may determine the emotion correlation equation by analyzing the emotion index.

The processor 150 may generate a virtual sound based on driving information (S240).

The processor 150 may generate the healing sound by designing the virtual sound based on the emotional status (S250). The processor 150 may re-design the virtual sound by utilizing the emotion correlation equation as feedback information.

The processor 150 may reproduce and output the healing sound (S260). The processor 150 may perform at least one of a vibration outputting operation, a scent outputting operation, or a light driving operation, in line to the healing sound.

Figure 7:
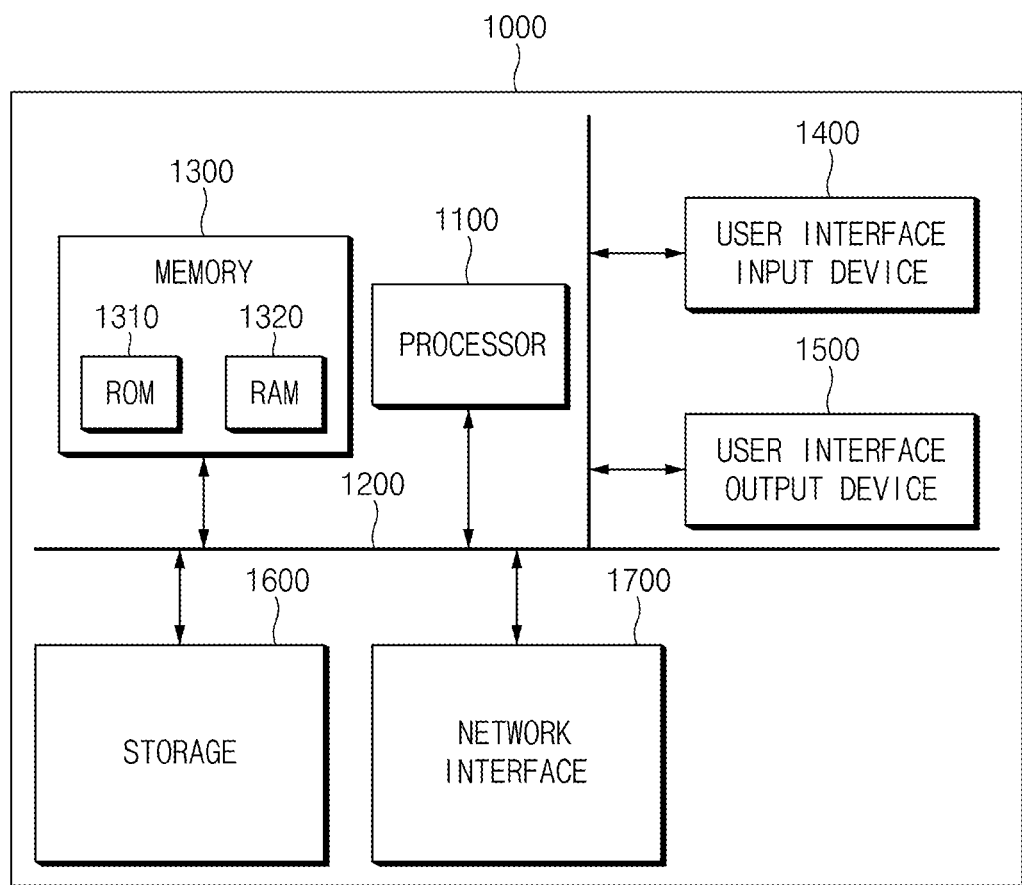
FIG. 7 is a block diagram illustrating a determining system to execute the method for caring emotion based on the vehicle sound, according to exemplary embodiments of the present invention.

FIG. 7 is a block diagram illustrating a computing system to execute the method for caring emotion based on the vehicle sound, according to exemplary embodiments of the present invention.

Referring to FIG. 7, a computing system 1000 may include at least one processor 1100, a memory 1300, a user interface input device 1400, a user interface output device 1500, a storage 1600, and a network interface 1700, which are connected to each other via a bus 1200.

The processor 1100 may be a central processing unit (CPU) or a semiconductor device configured for processing instructions stored in the memory 1300 and/or the storage 1600. Each of the memory 1300 and the storage 1600 may include various types of volatile or non-volatile storage media. For example, the memory 1300 may include a read only memory (ROM; see 1310) and a random access memory (RAM; see 1320).

Thus, the operations of the methods or algorithms described in connection with the exemplary embodiments included in various exemplary embodiments of the present invention may be directly implemented with a hardware module, a software module, or the combinations thereof, executed by the processor 1100. The software module may reside on a storage medium (i.e., the memory 1300 and/or the storage 1600), such as a RAM, a flash memory, a ROM, an erasable and programmable ROM (EPROM), an electrically EPROM (EEPROM), a register, a hard disc, a removable disc, or a compact disc-ROM (CD-ROM). The exemplary storage medium may be coupled to the processor 1100. The processor 1100 may read out information from the storage medium and may write information in the storage medium. Alternatively, the storage medium may be integrated with the processor 1100. The processor 1100 and storage medium may reside in an application specific integrated circuit (ASIC). The ASIC may reside in a user terminal. Alternatively, the processor 1100 and the storage medium may reside as separate components of the terminal of the user.

According to various exemplary embodiments of the present invention, the emotional status of the driver may be recognized based on the driving information and the body information, and the sense output may be controlled based on the recognized emotional status, providing the emotion care solution.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "forwards", and "backwards" are used to describe features of the exemplary embodiments with reference to the positions of such features as displayed in the figures. It will be further understood that the term "connect" or its derivatives refer both to direct and indirect connection.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the scope of the present invention be defined by the Claims appended hereto and their equivalents.

What is claimed is:

1. An apparatus of caring emotion of a driver based on a vehicle sound, the apparatus comprising:
   a detector configured to detect driving information of a vehicle and body information of the driver;
   a non-transitory storage configured to store instructions; and
   a processor electrically connected to the detector and the non-transitory storage and configured to execute the instructions,
   wherein the processor is configured to:
   determine an emotional status of the driver by use of at least one of the driving information or the body information;
   generating a healing sound by designing a virtual sound according to the driving information and the emotional status of the driver; and
   outputting the healing sound, and
   wherein the processor is configured to generate three emotion models by applying previously extracted personalized topics and emotions determined by a deep learning-based emotion analyzing algorithm.

2. The apparatus of claim 1, wherein the processor is configured to perform emotion modeling for modeling the emotion of the driver by utilizing the deep learning-based emotion analyzing algorithm.

3. The apparatus of claim 2, wherein the deep learning-based emotion analyzing algorithm is designed based on a conversational memory network (CMN).

4. The apparatus of claim 2, wherein the processor is configured to:
   determine emotion adjectives based on the generated three emotion models.

5. The apparatus of claim 4, wherein the personalized topics are extracted by utilizing a Latent Dirichelt Allocation (LDA) algorithm.

6. The apparatus of claim 4, wherein the processor is configured to determine the emotion adjectives using a Latent Semantic Analysis (LSA) algorithm and a Girvan-Newman algorithm.

7. The apparatus of claim 4, wherein the processor is configured to determine an emotion correlation equation by analyzing an emotion index based on the driving information and the determined emotion adjectives.

8. The apparatus of claim 7, wherein the processor is configured to analyze the emotion index using a convolutional neural network (CNN) algorithm.

9. The apparatus of claim 7, wherein the processor is configured to design the virtual sound by utilizing the emotion correlation equation as feedback information.

10. The apparatus of claim 7, wherein the emotion correlation equation is determined through a Multiple Regression Analysis (MRA) algorithm.

11. The apparatus of claim 1, wherein the processor is configured to perform at least one of vibration output, scent output, or light driving, in link to the healing sound.

12. A method for caring emotion of a driver based on a vehicle sound, the method comprising:
    detecting driving information of a vehicle and body information of the driver;
    determining, by a processor, an emotional status of the driver by use of at least one of the driving information or the body information;
    generating, by the processor, a healing sound by designing a virtual sound according to the driving information and the emotional status of the driver; and
    outputting, by the processor, the healing sound,
    wherein the method further includes performing of emotion modeling, and wherein the performing of the emotion modeling includes generating three emotion models by applying previously extracted personalized topics and emotions determined by a deep learning-based emotion analyzing algorithm.

13. The method of claim 12, further including:
    the performing of the emotion modeling for modeling the emotion of the driver by utilizing the deep learning-based emotion analyzing algorithm.

14. The method of claim 13, wherein the performing of the emotion modeling includes:
    extracting personalized topics by utilizing a Latent Dirichelt Allocation (LDA) algorithm;
    deriving emotions by analyzing the emotion by an emotion classifier, based on the extracted personalized topics; and
    deriving an emotion adjective based on the generated three emotion models.

15. The method of claim 14, wherein the deriving of the emotion adjective includes:
    deriving the emotion adjective using a Latent Semantic Analysis (LSA) algorithm and a Girvan-Newman algorithm.

16. The method of claim 14, further including:
    deriving an emotion correlation equation by analyzing an emotion index based on the driving information and the emotion adjective.

17. The method of claim 16, wherein the deriving of the emotion correlation equation includes:
    analyzing the emotion index using a convolutional neural network (CNN) algorithm.

18. The method of claim 16, wherein the generating of the healing sound includes:
   designing the virtual sound by utilizing the emotion correlation equation as feedback information.

19. The method of claim 18, wherein the designing of the virtual sound includes:
   performing at least one of pitch control, gain control, an APS control, frequency filtering, shepard layer control, or volume control for the virtual sound.

20. The method of claim 12, further including:
   performing, by the processor, at least one of vibration output, scent output, or light driving, in link to the healing sound.

* * * * *